United States Patent [19]
Darsow

[11] Patent Number: 6,124,443
[45] Date of Patent: Sep. 26, 2000

[54] PROCESS FOR THE HYDROGENATION OF SUGARS

[75] Inventor: Gerhard Darsow, Krefeld, Germany

[73] Assignee: Bayer Aktiengesellschaft, Leverkusen, Germany

[21] Appl. No.: 09/007,546

[22] Filed: Jan. 15, 1998

[30] Foreign Application Priority Data

Jan. 22, 1997 [DE] Germany .............................. 197 01 991

[51] Int. Cl.[7] .................................................. C07G 3/00
[52] U.S. Cl. ..................... 536/18.5; 536/4.1; 536/18.6; 536/124; 536/125; 568/861; 568/862; 568/863
[58] Field of Search ........................... 536/4.1, 124, 125, 536/18.5, 18.6; 568/861, 862, 863

[56] References Cited

U.S. PATENT DOCUMENTS

| | | | |
|---|---|---|---|
| 3,741,776 | 6/1973 | Mitsuhashi et al. | 99/141 |
| 4,322,569 | 3/1982 | Chao et al. | 568/863 |
| 4,382,150 | 5/1983 | Arena . | |
| 4,433,184 | 2/1984 | Huibers et al. | 568/863 |
| 4,608,446 | 8/1986 | Möhring et al. | 568/863 |
| 5,162,517 | 11/1992 | Darsow . | |
| 5,170,578 | 12/1992 | Pampel | 40/316 |
| 5,550,220 | 8/1996 | Meyer et al. | 536/18.5 |
| 5,641,872 | 6/1997 | Darsow | 536/18.5 |
| 5,684,215 | 11/1997 | Horn et al. . | |

FOREIGN PATENT DOCUMENTS

| | | |
|---|---|---|
| 0421196 | 4/1991 | European Pat. Off. . |
| 0423525 | 4/1991 | European Pat. Off. . |
| 544666 | 2/1932 | Germany . |
| 554074 | 6/1932 | Germany . |
| 4416408 | 11/1995 | Germany . |
| 1236910 | 6/1971 | United Kingdom . |

OTHER PUBLICATIONS

Wolfrom et al., "Crystalline Lactositol", *Crystalline Lactositol*, Mar., 1938 pp. 571–573.

Nelsen et al., "Determination of Surface Area: Adsorption Measurements by a Continuous Flow Method", *Analyst. Chem.*, vol. 30, No. 8, Aug. 1958, pp. 1387–1390.

*Primary Examiner*—James O. Wilson
*Attorney, Agent, or Firm*—Norris, McLaughlin & Marcus, P.A.

[57] ABSTRACT

Epimer-free sugar alcohols can be prepared from the corresponding sugars by catalytic hydrogenation with hydrogen in aqueous solution, the hydrogenation being carried out continuously at a hydrogen pressure of 100 to 400 bar and a reaction temperature of 20 to 70° C. on support-free shaped bodies which are arranged in a fixed bed and are made of pressed powders of metals or alloys of the elements of the iron subgroup of subgroup VIII of the Periodic Table of the Elements together with elements of subgroup IV and/or V. The shaped bodies have a compressive strength of 20 to 220 N and an internal surface area of 10 to 100 $m^2/g$.

18 Claims, No Drawings

PROCESS FOR THE HYDROGENATION OF SUGARS

BACKGROUND OF THE INVENTION

1. Field of the Invention

The invention relates to an inexpensive process for the continuous catalytic hydrogenation of sugars, such as D-xylose, α-D-glucose, 4-O-β-D-galactopyranosyl-α-D-glucopyranose or 4-O-α-D-glucopyranosyl-α-D-glucopyranose, with hydrogen to give the corresponding sugar alcohols, such as D-xylitol, D-sorbitol, 4-O-β-D-galactopyranosyl-α-D-sorbitol or 4-O-α-D-glucopyranosyl-α-D-sorbitol.

The course of the reaction is given by the following reaction schemes:

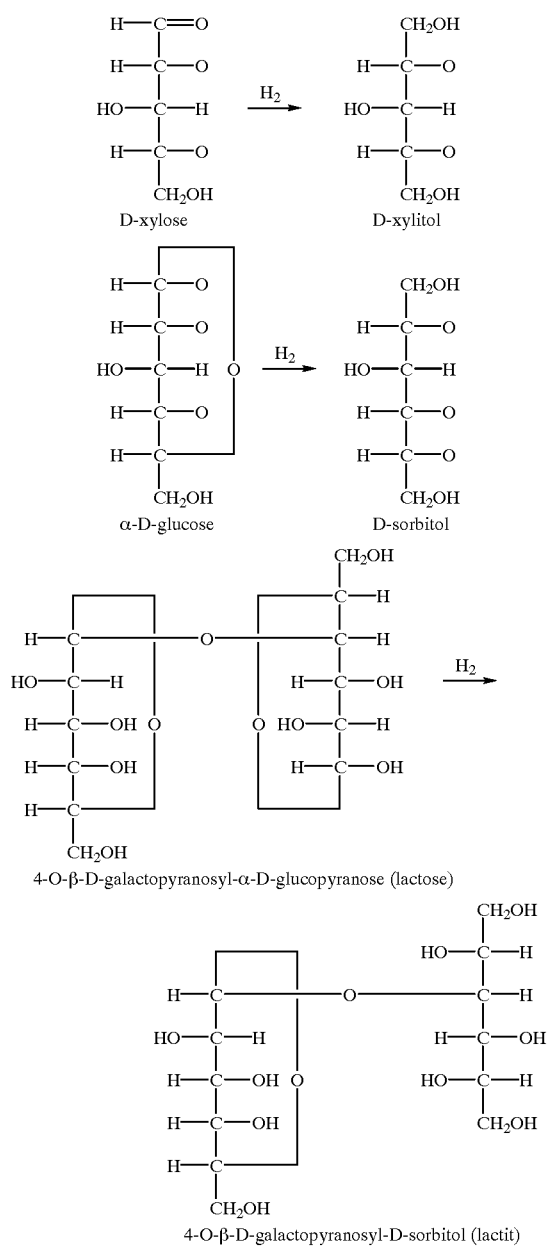

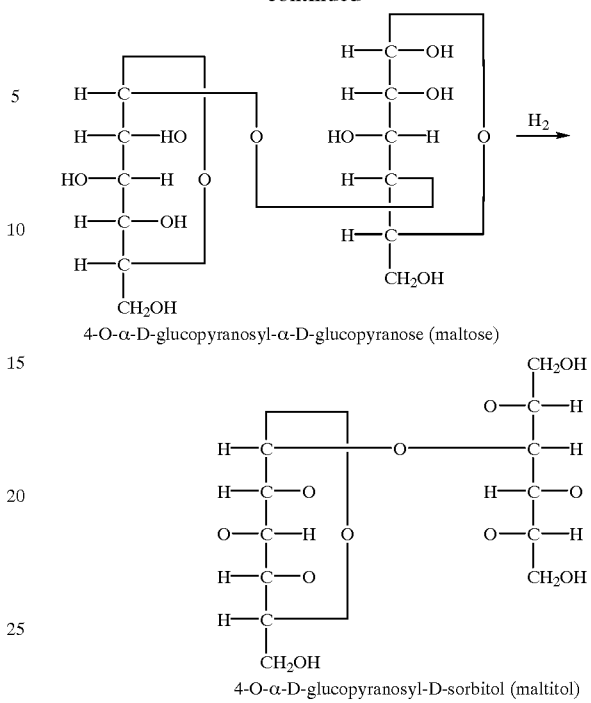

2. Description of the Related Art

To prepare xylitol (DE-A 19 35 934) or sorbitol (DE-C 544 666; DE-C 554 074), hitherto, use has principally been made of a batch process in which a pulverulent nickel catalyst is used in a suspension process. To prepare lactitol, which has not hitherto been detected in nature, EP-A 39 981 also discloses a batch process in which likewise a pulverulent nickel catalyst is used in a suspension process. A process of this type is also proposed in U.S. Pat. No. 3,741,776 for the preparation of maltitol.

Batch suspension processes have the disadvantage that their capacity, relative to the reaction volume, is very low and there is thus a need for high-volume expensive reaction apparatuses and storage tanks. The energy consumption is uneconomic and the labour requirements are relatively high. Continuous powder catalyst processes which operate with two or more batch hydrogenation reactors connected in cascade only partially avoid said disadvantages. There is still the laborious task of specifically metering the pulverulent catalyst, activating it, circulating it by pumping and quantitatively filtering it off from the reaction product. The catalyst pumps are subject to high mechanical stress. Quantitative removal of the pulverulent catalyst is complex (alternating coarse and fine filtration apparatuses). In addition, there is a high risk that the catalyst relatively rapidly loses its activity due to the additional operations (high catalyst consumption). It is therefore desirable to make the reaction proceed on fixed-bed cataysts, which should have a high specific activity which as far as possible should not decay even over a prolonged period of several years, since frequent changes of catalyst in fixed-bed reactions would also be expensive. In the case of fixed-bed catalysts, also, it has been conventional hitherto to connect a plurality of reactors one after the other, which gives a plurality of series-connected reaction zones (German Offenlegungsschrift 3 214 432).

Use is predominantly made here of nickel catalysts on oxidic support material ($SiO_2/Al_2O_3$) having extremely high active surface areas of 140 to 180 m$^2$/g, so that the catalysts in the initial phase are frequently so active that they must be stabilized by additional chemical treatment methods, for example by treatment with oxygen gas to form monomolecular oxygen layers on the catalyst surface (German Offenlegungsschrift 3 110 493). However, the deactivating stabilization of the catalyst then requires reaction temperatures in the hydrogenation which are so high (130 to 180° C.) that uncontrollable side reactions become possible, such as discoloration by caramelization and hydrogenating cracking (hydrogenolysis) of the sugar alcohols to the formation of methanol and even methane. In addition, in this mode of reaction, relatively large amounts of heavy metals constantly pass into solution in ionic or colloidal form which, on the one hand, requires subsequent activated carbon treatment of the hydrogenated product and, on the other hand, requires deionization by ion exchangers.

Since most hydrogenation processes operate with sugar solutions set to pHs of 7 to 13, the acidic starting solutions must be admixed with alkali metals or alkaline earth metals, which likewise must be laboriously removed again (German Offenlegungsschrift 3 110 493; German Offenlegungsschrift 3 214 432). In addition, a marked epimerization would be expected under the hydrogenation conditions, so that, for example, D-xylose would also produce, in addition to xylitol, lyxitol (or arabinitol and ribitol). α-D-Glucose, in addition to sorbitol, would also be expected to produce mannitol. In addition, the effect of cleaving the carbon chain of sugars during the catalytic hydrogenation by Raney nickel is known; German Offenlegungsschrift 2 756 270 describes the effect on a sugar mixture, as originates from the self-condensation of formaldehyde, a marked shift from higher C chain numbers to lower C chain numbers being observed in the illustrative examples given there.

EP-A 423 525 (a counterpart of U.S. Pat. No. 5,162,517) discloses a process for the continuous hydrogenation of sugars to the corresponding epimer-free sugar alcohols on support-free solid bodies of elements of the iron subgroup of subgroup VIII of the Periodic Table of the Elements, these support-free shaped bodies preferably having been prepared by pressing and/or bonding metal powders. In this case it was found that the sugars are not only substantially converted, but chiefly only one sugar alcohol in each case is produced with substantial avoidance of epimerization and C-chain cleavage and with avoidance of the formation of higher-molecular components by condensation reaction with ether formation.

EP-A 694 515 discloses a more inexpensive process for the preparation of sugar alcohols selected from the group consisting of xylitol, sorbitol, 4-O-β-D-galactopyranosyl-α-D-sorbitol (lactitol) and 4-O-α-D-glucopyranosyl-α-D-sorbitol (maltitol) by catalytic hydrogenation of the corresponding sugars D-xylose, α-D-glucose, 4-O-β-D-galactopyranosyl-α-D-glucopyranose and 4-O-α-D-glucopyranosyl-α-D-glucopyranose, repectively, on support-free shaped bodies made of elements of the iron subgroup of subgroup VIII. of the Periodic Table of the Elements including activating elements of subgroup VI. However, it continues to be desirable to increase the low conversion rates (g of sugar /1 of catalyst×h) and to further reduce the catalyst costs. Furthermore, the aim is still to carry out a process in as high a concentration as possible of the substance to be hydrogenated in the solvent and at a temperature as low as possible in order to decrease further the energy costs also.

SUMMARY OF THE INVENTION

Surprisingly, it has now been found that metal powders of nickel, cobalt and iron or their alloys which contain elements of subgroup IV. and/or subgroup V. of the periodic table, after they are pressed to give shaped bodies, not only catalyze equally well the hydrogenation of said sugars to epimer-free sugar alcohols, but catalysts of these metals or metal alloys, which are 50 to 70% cheaper than catalysts made of the pure elements of subgroup VIII, even have a still higher hydrogenation activity, so that the hydrogenation reaction can be carried out at a reaction temperature lower by up to 50° C., or that the hourly catalyst loading can be increased by up to 50% in comparison with earlier results. The powders used can additionally include certain proportions (max. admissible 20% by weight) of other non-catalytic metals or metal alloys (eg. manganese, silicon, aluminum), without the high activity being decreased.

The invention therefore relates to a process for the preparation of epimer-free sugar alcohols selected from the group consisting of xylitol, sorbitol, 4-O-β-D-galacopyranosyl-α-D-sorbitol (lactitol) and 4-O-α-D-glucopyranosyl-α-D-sorbitol (maltitol) by catalytic hydrogenation of the corresponding sugars D-xylose, α-D-glucose, 4-O-β-D-galactopyranosyl-α-D-glucopyranose and 4-O-α-D-glucopyranosyl-α-D-glucopyranose, respectively, in aqueous solution with hydrogen under elevated pressure and at elevated temperature, which comprises carrying out the hydrogenation continuously at a hydrogen pressure of 100 to 400 bar, preferably 150 to 300 bar, and temperatures of 20 to 70° C., preferably 40 to 65° C., in the fixed-bed process in a reaction zone on support-free shaped bodies which serve as hydrogenation catalysts and have a compressive strength of 20 to 220 N, preferably 70 to 140 N, and an internal surface area of 10 to 100 m$^2$/g made of (i) one or more elements of the iron subgroup of subgroup VIII of the Periodic Table of the Elements (Mendeleev) which is (are) additionally alloyed with (ii) activating elements of subgroup IV. and/or subgroup V.

DETAILED DESCRIPTION OF THE INVENTION

The compressive strength of the support-free shaped bodies can be determined as specified by DIN 50 106. The support-free shaped bodies can be tested for the claimed internal surface areas and thus for usability in the process according to the invention by methods which have been described by F. M. Nelsen and F. T. Eggertsen, Analyt. Chem. 30 (1958), 1387 and S. J. Gregg and S. W. Sing, Adsorption, Surface Area and Porosity, London 1982, chapters 2 and 6.

The iron subgroup of subgroup VIII. of the Periodic Table includes the elements iron, cobalt and nickel. The support-free shaped bodies to be used according to the invention include one or more of these metals in amounts of at least 50% by weight, preferably at least 60% by weight, in particular at least 70% by weight, based on the total weight of the support-free shaped bodies. Preferred ferrous metals are Fe and Ni.

Subgroup IV of the Periodic Table includes the element titanium, zirconium and hafnium. Subgroup V of the Periodic Table includes the elements vanadium, niobium and tantalum. The support-free shaped bodies to be used according to the invention include one or more of these metals in amounts of at least 1.5% by weight, preferably at least 3.0% by weight, in particular at least 6.0% by weight, based on the total weight of the support-free shaped bodies; they include one or more of these metals in amounts of at most 30% by weight, preferably at most 20% by weight, and in particular at most 15% by weight, based on the total weight of the support-free shaped bodies. Preferred elements among those mentioned are Ti, Zr and V.

The support-free shaped bodies to be used according to the invention can, in addition, include—in each case based on the total weight of the support-free shaped bodies—up to 20% by weight, preferably up to 15% by weight, of other metals. Their lower limit can accordingly be 0% by weight. Examples of such metals, which need not be catalytically active, include aluminum, silicon and manganese. According to a preferred embodiment, the support-free shaped bodies contain, in addition to the components (i) and (ii), no more than 15% by weight of aluminum and/or no more than 5% by weight of other metals.

The support-free shaped bodies can be prepared by conventional methods by pressing the metal powders under high pressure, for example on tableting or pelleting machines; to improve the adherence of the metal particles, graphite and/or adhesives can also be used in amounts of 0.5 to 1% by weight, based on the total weight of the constituents forming the catalyst. The support-free shaped bodies are preferably prepared in an oxygen-free atmosphere, in order to avoid surface oxidation. Examples of shaped bodies are tablets, balls, granules having diameters of 2 to 10 mm, preferably 3 to 7 mm. Tableted shaped bodies can, in addition, be furnished with an axial borehole to increase the external surface area. Shaped bodies of this type have a smooth surface, considered macroscopically. The shaped bodies to be used according to the invention have compressive strengths of 20 to 220 N, preferably 70 to 140 N. This is important, since lower compressive strengths lead to disintegration or erosive wear of the shaped bodies, which would cause an undesirable contamination of the reaction product with metal powder.

As starting compound for the process according to the invention, this can be made of crystalline D-xylose, α-D-glucose, α-lactose or α-lactose monohydrate or maltose (liquid or also, in its β form, crystalline monohydrate). The starting material is preferably dissolved in oxygen-free deionized water in such a manner that a 40 to 60% strength by weight, preferably 45 to 55% strength by weight, solution is formed whose pH is 4.5 to 11.5. The solution of the monosaccharides is preferably adjusted to a pH of 4.5 to 9.5, and that of the disaccharides preferably to a pH of 5.5 to 10.5. For all starting materials, the particularly preferred pH range is 6 to 8.0. The sugars mentioned as starting compounds exhibit, dissolved in water having a pH of 7, a neutral reaction, or due to trace formation of sugar acids, a weakly acidic reaction, but can be adjusted to the desired pH, for example, by targeted addition of basic water-soluble compounds, such as ammonium carbonates or, preferably, ammonia in aqueous solution, or of acidic compounds, such as sugar acids, sorbic acid or citric acid.

For the process according to the invention, use is made of pure hydrogen which is precompressed to a pressure of 100 to 400 bar, preferably 150 to 300 bar. The amount of $H_2$ is 2–100 times the stoichiometric amount, preferably 4–50 times. The hydrogenation is performed continuously in the fixed-bed process on the support-free shaped bodies serving as hydrogenation catalysts by passing the solution to be hydrogenated over the catalyst provided in a hydrogenation reactor either co-currently ascending from the bottom together with the previously admixed hydrogen (co-current process), or conducting the solution to be hydrogenated which ascends from the bottom in the opposite direction to hydrogen flowing in from the top (countercurrent process). The hydrogenation reactor can be either an individual high-pressure tube made of steel or a steel alloy which is wholly or partially filled with the support-free shaped bodies, in which case at certain tube cross-sections, employing the support-free shaped bodies on holders (wire baskets or the like) can be useful, or a jacketed high-pressure tube bundle, the individual tubes of which are wholly or partially filled with support-free shaped bodies. Furthermore, instead of a relatively large single-tube reactor, a fully continuous arrangement of a plurality of small single reactors can be operated in succession in a cascade or in parallel.

The hydrogenation is carried out at temperatures of 20 to 70° C., preferably 40 to 65° C. Lower temperatures would mean longer residence times or abandoning a substantially quantitative conversion of the sugars. Higher temperatures lead to uncontrollable side reactions, such as caramelization, ether cleavage or hydrogenating cracking, which can lead to discoloration and formation of undesirable by-products. The hourly catalyst loading can be 250 to 750 g of the sugars mentioned as starting compounds per liter of catalyst. When said reaction conditions are complied with, at such loadings unexpectedly high catalyst service lives of 20,000 hours and more may be achieved, in which case specific catalyst consumptions of 0.1% by weight or less are achieved.

The process according to the invention permits the sugar alcohols to be prepared at a purity of greater than 99.5% in the dry matter. The content of unreacted sugars reaches values of $\leq 0.2\%$. The commerically conventional specifications for the sugar alcohols, for instance according to the Deutsches Arzneimittelbuch DAB, the United States Pharmacopeia USP or the Food Chemical Codex FCC, can therefore be met directly readily and without further purification processes.

The technical advantages of the process according to the invention are, in addition to the high yield due to the virtually quantitative conversion and the ecological advantages given by the purity of the product prepared, thus the extremely low catalyst consumption, the low catalyst costs, the low energy costs and the extremely high hourly catalyst load capacities, which lead to high space-time yields.

The aqueous sugar alcohol solution leaving the reactor, after depressurization, in which the excess hydrogen can be collected and, after compression and supplementation by further hydrogen, reused, can already be used as sugar substitute in liquid form. The water of this solution may be removed in various ways, for example via pray-dryers, roller dryers or by freeze-drying. It has proved to be expedient to concentrate the resulting generally glass-clear sugar alcohol solution to a sugar alcohol content of about 70 to 80% by weight in a falling-film evaporator or a similarly functioning apparatus and then, after further evaporation in a vacuum crystallization apparatus, with cooling to bring it to partial or complete crystallization. The crystals may be brought to a uniform particle size by a downstream grinding process and possibly screening. The resulting products are free-flowing.

Xylitol has a melting point of 94° C. In the case of sorbitol, depending on the crystallization conditions, various crystal modifications can be produced, of which the γ form having a melting point of 101° C. is the most stable. Depending on the crystallization conditions, lactitol can be produced either as dihydrate having a melting point of 78° C. or as monohydrate having a melting point of 123° C. The solubilities of the two hydrates in water differ; the monohydrate is less soluble than the dihydrate. The hydrates are non-hygroscopic and therefore have technological advantages over other polyols. Anhydrous lactitol can be isolated in crystalline form from solutions in absolute ethanol. It melts at 146° C. and is non-hygroscopic. Anhydrous maltitol can be isolated as crystalline powder from solutions in absolute ethanol after seeding with seed crystals. It melts at 146° C. and is hygroscopic (J. Am. Chem. Soc. 60 (1938), 571). All sugar alcohols prepared according to the invention have a catalyst constituent content of less than 3 ppm; they are generally epimer-free.

Epimer-free in the context of the present invention is taken to mean having a content of epimers which is negligible for the purity of said sugar alcohols to the extent that these sugar alcohols comply with the commerically conventional specifications, as given in the DAB or in the USP and FCC, without further purification operations.

The sugar alcohols are obtained in virtually quantitative yield in the process according to the invention. This is of particular importance, since removing higher-molecular interfering impurities (resulting from ether formation) or lower-molecular interfering impurities (resulting from hydrogenolysis) from the reaction product by additional purification processes, such as recrystallization from solvents, usually demands considerable ecological costs with respect to their disposal. The xylitol epimer sugar alcohols of the lyxitol type (or arabinitol and ribitol) are present in the reaction product at most in traces (<0.1% by weight). The diastereomer of lactitol, 4-O-β-D-galactopyranosyl-α-D-mannitol, and the diastereomer of maltitol, 4-O-α-D-glucopyranosyl-α-D-mannitol, are not detectable in the respective reaction product.

The oxygen-free and support-free fixed-bed catalysts to be used according to the invention, in contrast to the supported catalysts, do not have a tendency to "bleed", i.e. do not have a tendency to transfer catalyst constituents in ionic or colloidal form into the solution phase of the substrate, so that the substrate does not become contaminated by heavy metals, which usually likewise can only be removed from the substrate with difficulty, for example using ion exchangers. The catalyst metals to be used can after their use be readily reprocessed and reused, since the heavy metals do not have to be laboriously removed from a support material. In addition, in the case of polyhydroxyl compounds, there would be the risk of the tendency to form with heavy metal ions complex chelate compounds which can only be removed with difficulty from the sugar alcohol solutions.

The sweetening power of xylitol reaches about 80 to 100% of the sweetening power of sucrose. Because of its pleasant taste, xylitol is suitable as a sugar substitute in the diabetic diet and as a non-cariogenic sweetener in confectionery and oral pharmaceuticals. Xylitol is permitted for use in diabetic foods by the German Dietary Regulation (Bundesgesetzblatt [German Federal Law Gazette] 1, 1982, page 71; cited in Ullmann, 4th Edition, Volume 24, p. 777, literature reference [209]) in unrestricted amounts. Xylitol is particularly suitable for manufacturing confectionery, such as sweets and chewing, gum (Swiss Dent. 1, (7/8) 1980, pages 25 to 27; cited in Ullmann, 4th Edition, Volume 24, p. 777, literature reference [223]). Products for treating the oral and throat cavity, such as toothpastes, antiseptic throat tablets, cough sweets, are also increasingly being sweetened with xylitol (Swiss Dent. 3, (7/8) 1982, pages 25 to 30; cited in Ullmann, 4th Edition, Volume 24, p. 777, literature reference [224]).

The sweetening power of sorbitol reaches about 50 to 60% of the sweetening power of sucrose. To increase the sweetening power, the aqueous solution can be admixed with synthetic sweeteners, for example with cyclohexyl sulfamate or aspartylphenylalanine methyl ester, and iso-lated in crystalline form by concurrent vacuum crystallization. However, the synthetic sweeteners can also be mixed in solid form with the sorbitol crystals. Sorbitol can also be mixed in liquid or solid form with other sweet-tasting sugar alcohols, for example with xylitol, maltitol, lactitol and others. Sorbitol is only absorbed in the human body to a minor extent, and only this amount is metabolized. Therefore, sorbitol is suitable as a sugar substitute for diabetics and as a low-calorie sweetener. In addition, it is less cariogenic than sucrose or other sugars.

Lactitol is not metabolized as carbohydrate in the human body and is neither hydrolyzed nor absorbed in the small intestine. Therefore, lactitol is suitable as a sugar substitute for diabetics. In addition, it is less cariogenic than sucrose. The sweetening power of lactitol reaches about 40% of the sweetning power of sucrose. To increase the sweetening power, the aqueous solution, as is the case with sorbitol, can be admixed with synthetic sweeteners and isolated in crystalline form by concurrent vacuum crystallization. However, the synthetic sweeteners can also be mixed in solid form with the lactitol crystals. Furthermore, lactitol can be mixed in liquid or solid form with other sweet-tasting, sugar alcohols, for example with sorbitol, xylitol and others.

Maltitol is only metabolized with difficulty in the human body by amylolytic enzymes. Maltitol is therefore suitable as a sugar substitute for a reduced-calorie diet and for diabetics (Ullmanns Encyclopadie der technischen Chemie [Ullmann's Encyclopedia of Industrial Chemistry], 4th Edition, Volume 24, Weinheim 1983, p. 771). The sweetening power of maltitol reaches the sweetening power of sucrose. Maltitol can be mixed in liquid form with other sweet-tasting sugar alcohols, for example with sorbitol, xylitol and others. It can be particularly recommended for use in the beverage industry because of its high sweetening power and low tendency to crystallization, even in high concentrations.

Toxic effects of xylitol, sorbitol and lactitol have not been found, even in long-term studies (Ullmanns Encyclopadie der technischen Chemie[Ullmann's Encyclopedia of Industrial Chemistry], 4th Edition, Volume 24, Weinheim 1983, p. 779), so that varied applications in the food sector, in the production of diabetic products and of sugar-free confectionery and foods having a low nutritive value come about. In the case of maltitol also, no toxic effects were found in long-term studies.

EXAMPLES

The percentages in the examples below are by weight.

Example 1

A vertically upright heat-insulated high-pressure tube made of stainless steel of internal diameter 45 mm and length 1 m was packed witht 1.4 l of a hydrogenation catalyst prepared by tableting a metal powder of an Ni/Zr alloy having a Zr content of 12.8%, which catalyst, at a cylinder height of 5 mm and a diameter of 5 mm, had a compressive strength of 109 N on the curved cylinder surface and an internal surface area of 74 m$^2$/g. 450 ml of a 45% strength solution of D-xylose in demineralized oxygen-free drinking water having a pH of 7.0 were continuously pumped per hour through this tube, ascending from bottom to top, together with five times the molar amount of high-purity hydrogen at a pressure of 300 bar.

Aqueous solution and hydrogen were passed together beforehand through a heat exchanger and heated in such a manner that they entered the high-pressure tube at a temperature of 60° C. The mixture of aqueous solution and excess hydrogen leaving the high-pressure tube was passed via a cooler into a separator from where the hydrogen, after replacing the amount consumed, was pumped back into the preheater, together with fresh D-xylose solution and from there back into the high-pressure tube. The colorless and clear aqueous solution was depressurized and concentrated in a falling-film evaporator to a sugar alcohol content of approximately 75% and then crystallized after further evaporation in a vacuum crystallizer with cooling. A white, slightly hygroscopic, odorless solid product was obtained, which was processed to give a fine crystalline powder. The xylitol formed was otherwise highly pure and, in the stable rhombic crystal form, had a melting point of 94° C. The content of non-hydrogenated D-xylose was <0.1%. Ni and Zr contents were each $\leq 1$ ppm. The activity of the catalyst was unchanged even after a running time of 1852 hours.

Example 2

Through a high-pressure tube as in Example 1, but made of high-pressure steel N9, the hydrogen was passed in the reverse direction of reaction flow as in Example 1, in the opposite direction to the ascending solution of D-xylose, at a temperature of 60° C. and a hydrogen pressure of 300 bar, the same amount of a 45% strength aqueous solution of D-xylose which had a pH of 7.0 being hydrogenated per hour. The catalyst had been produced by tableting metal powder of a Ni/Zr alloy having a Zr content of 14.9%, additionally alloyed with an Al content of 10.5%. The tablets, at a cylinder height of 5 mm and a diameter of 5 mm, had a compressive strength of 75 N on the curved cylinder surface and an internal surface area of 81 $m^2/g$. After a running, time of 2224 hours with undiminished activity, the conversion rate of D-xylose was $\geq 99.8\%$. The completely crystallized xylitol, which had a purity of $\geq 99.6\%$, had a non-hydrogenated D-xylose content of 0.1%. Ni, Zr and Al contents were each 2 ppm.

Example 3

In a high-pressure tube as in Example 1, the same amount per hour of a 45% strength aqueous solution of D-xylose which had a pH of 7.5 was hydrogenated in the same manner as in Example 1 at a temperature of 60° C. and a hydrogen pressure of 300 bar. The catalyst had been produced by tableting an Ni/Fe/Zr alloy. The alloy had an Fe content in Ni of 5% and a Zr content of 10.9%. The tablets, at a cylinder height of 5 mm and a diameter of 5 mm, had a compressive strength of 107 N on the curved cylinder surface and an internal surface area of 93 $m^2/g$. The crystalline xylitol produced in a vacuum crystallizer with seeding by seed crystals had a purity of $\geq 99.6\%$. The content of unreacted D-xylose was 0.1%. Ni, Fe and Zr contents were each <1 ppm. The activity of the catalyst was unchanged after a running, time of 1620 hours.

Example 4

In a high-pressure tube as in Example 1,400 ml of a 45% strength aqueous solution of D-xylose which had a pH of 6.5 were hydrogenated per hour in the same manner as in Example 1 at a temperature of 60° C. and a hydrogen pressure of 300 bar. The catalyst was produced by tableting a pulverized Ni/Zr alloy and a pulverized Ni/Ti alloy and had a Zr content of 12.1% and a Ti content of 5.8%. The tablets, at a cylinder height of 5 mm and a diameter of 5 mm, had a compressive strength of 103 N on the curved cylinder surface and an internal surface area of 81 $m^2/g$. The xylitol produced in a rotary vacuum tube had a content of unreacted D-xylose of $\leq 0.1\%$. The Ni, Zr and Ti contents were each <1 ppm. The activity of the catalyst was still undiminished after a running time of 1140 hours.

Example 5

A high-pressure tube as in Example 1 was packed with 1.41 of a hydrogenation catalyst produced by tableting metal powder comprising an Ni/Zr/Al alloy having a Zr content of 14.9%, which hydrogenation catalyst, at a cylinder height of 5 mm and a diameter of 5 mm, had a compressive strength of 75 N on the curved cylinder surface and an internal surface area of 81 $m^2/g$. 450 ml of a 45% strength solution of α-D-glucose in demineralized oxygen-free drinking water having a pH of 7.0 were continuously pumped per hour through this tube, ascending from bottom to top, together with ten times the molar amount of high-purity hydrogen at a pressure of 300 bar. Aqueous solution and hydrogen were passed together beforehand through a heat exchanger and heated in such a manner that they entered the high-pressure tube at a temperature of 60° C. The mixture of aqueous solution and excess hydrogen leaving the high-pressure tube was passed via a cooler into a separator, from where hydrogen, after replacement of the amount consumed, was pumped back into the preheater, together with fresh α-D-glucose solution and from there back into the high-pressure tube. The colorless and clear aqueous solution was depressurized and concentrated in a falling-film evaporator to a sugar alcohol content of approximately 70% and then crystallized after further evaporation in a vacuum crystallizer with cooling. A white, slightly hygroscopic, odorless solid product was obtained which was ground to give a fine crystalline powder. The sorbitol formed was otherwise highly pure and in the stable γ form had a melting point of 101° C. The content of non-hydrogenated α-D-glucose was $\leq 0.1\%$. Ni, Zr and Al contents were each <1 ppm. The activity of the catalyst was unchanged even after a running time of 2622 hours.

Example 6

Through a high-pressure tube as in Example 1, the hydrogen was passed in the reverse direction of reaction flow as described in Example 1, in the opposite direction to the ascending solution of α,-D-glucose at a temperature of 60° C. and a hydrogen pressure of 300 bar, the same amount as in Example 1 of 45% strength aqueous solution of α-D-glucose which had a pH of 7.0 being hydrogenated per hour. The catalyst had been produced by tableting a metal powder of an Ni/Zr/Al alloy having a Zr content of 14.8% and an Al content of 10.5%. The tablets, at a cylinder height of 5 mm and a diameter of 5 mm, had a compressive strength of 75 N on the curved cylinder surface and an internal surface area of 81 $m^2/g$. After a running time of 1842 hours with undiminished activity, the conversion rate of α-D-glucose was 99.9%. The content of non-hydrogenated α-D-glucose in the sorbitol which crystallized out and had a purity of $\geq 99.7\%$ was <0.1%. The Ni content was <1 ppm. The Zr and Al contents were each <2 ppm.

Example 7

In a high-pressure tube as in Example 1, the same amount of a 40% strength aqueous solution of α-D-glucose which had a pH of 7.5 was hydrogenated per hour in the same manner as in Example 1 at a temperature of 55° C. and a hydrogen pressure of 300 bar. The catalyst had been produced by tableting a pulverized Ni/Fe/Zr alloy. The alloy had an Fe content in Ni of 5% and a Zr content of 10.9%. The tablets, at a cylinder height of 5 mm and a diameter of 5 mm, had a compressive strength of 107 N on the curved cylinder surface and an internal surface area of 93 m$^2$/g. The crystalline sorbitol produced in a vacuum crystallizer had a purity of ≧99.6%. The content of unreacted α-D-glucose was 0%. Ni, Zr and Fe contents were each <1 ppm. The activity of the catalyst was still unchanged after a running time of 1448 hours.

Example 8

In a high-pressure tube as in Example 1,400 ml of a 45% strength aqueous solution of α-D-glucose which had a pH of 6.5 were hydrogenated per hour in the same manner as in Example 1 at a temperature of 60° C. and a hydrogen pressure of 300 bar. The catalyst had been produced by tableting metal powder of an Ni/Zr/V alloy having a Zr content of 10.9% and a V content of 3.4%, and which additionally had an Al content of 10.1%. The tablets, at a cylinder height of 5 mm and a diameter of 5 mm, had a compressive strength of 109 N on the curved cylinder surface and an internal surface area of 81 m$^2$/g. The sorbitol produced in a rotary vacuum tube had a content of unreacted α-D-glucose of ≦0.1%. Ni, Zr, V and Al contents were each 1 ppm. The, activity of the catalyst was still undiminished after a running time of 1662 hours.

Example 9

A high-pressure tube as in Example 1 was packed with 1.41 of a hydrogenation catalyst produced by tableting metal powder comprising an Ni/Zr alloy having a Zr content of 14.9%, which hydrogenation catalyst, at a cylinder height of 3 mm and a diameter of 3 mm, had a compressive strength of 85 N on the curved cylinder surface and an internal surface area of 85 m$^2$/g. 500 ml of a 40% strength solution of 4-O-β-D-galactopyranosyl-α-D-glucopyranose in demineralized oxygen-free drinking water having a pH of 7.0 were continuously pumped per hour through this tube ascending from bottom to top together with ten times the molar amount of high-purity hydrogen at a pressure of 300 bar. Aqueous solution and hydrogen were passed together beforehand through a heat exchanger and heated in such a manner that they entered the high-pressure tube at a temperature of 60° C. The mixture of aqueous solution and excess hydrogen leaving the high-pressure tube was passed via a cooler into a separator, from where the hydrogen, after replacement of the amount consumed, was pumped back into the preheater, together with fresh 4-O-β-D-(galactopyranosyl-α-D-glucopyranose, and from there pumped back into the high-pressure tube. The colorless and clear aqueous solution was depressurized and concentrated in a falling-film evaporator to a sugar alcohol content of approximately 80% and then crystallized after further evaporation in a vacuum crystallizer with cooling. Depending on the crystallization conditions and the residual water content of the evaporated solution, this allowed the isolation of either the dihydrate having a melting point from 77 to 78° C. or of the monohydrate having a melting point from 122 to 123° C.; the resulting 4-O-β-D-galactopyranosyl-α-D-sorbitol was otherwise pure (purity ≧99.7%). The content of non-hydrogenated 4-O-β-D-galactopyranosyl-α-D-glucopyranose was ≦0.1%. The content of sorbitol was ≦0.1%. 4-O-β-D-Galactopyranosyl-D-mannitol and mannitol were not detected. Ni and Zr contents were each 1 ppm. The activity of the catalyst was unchanged even after a running time of 1880 hours.

Example 10

Through a high-pressure tube as in Example 1, the hydrogen was passed in the reverse direction of reaction flow as described in Example 1, in the opposite direction to the ascending solution of 4-O-β-D-galactopyranosyl-α-D-glucopyranose, at a temperature of 65° C. and a hydrogen pressure of 250 bar, the same amount as in Example 1 of 40% strength aqueous solution of 4-O-β-D-galactopyranosyl-α-D-glucopyranose which had a pH of 6.5 being hydrogenated per hour. The catalyst was produced by tableting from metal powder of an Ni/Zr/Al alloy having a Zr content of 10.9% and an Al content of 10.5%. The tablets, at a cylinder height of 5 mm and a diameter of 5 mm, had a compressive strength of 78 N on the curved cylinder surface and an internal surface area of 81 m$^2$/g,. After a running time of 1912 hours with undiminished activity, the content of 4-O-β-D-galactopyranosyl-β-D-sorbitol of the reaction mixture evaporated to dryness in a rotary evaporator was 99.6%. The content of non-hydrogenated 4-O-β-D-galactopyranosyl-α-D-glucopyranose was ≦0.1%. The content of sorbitol was 0.1%. 4-O-β-D-Galactopyranosyl-D-mannitol and mannitol were not detected. Ni, Zr and Al contents were each <3 ppm.

Example 11

In a high-pressure tube as in Example 1, the same amount of a 40% strength aqueous solution of 4-O-β-D-galactopyranosyl-α-D-glucopyranose which had a pH of 7.5 was hydrogenated per hour in the same manner as in Example 1 at a temperature of 65° C. and a hydrogen pressure of 300 bar. The catalyst had been produced by tableting as pulverized Ni/Zr/V/Al alloy. The alloy had a Zr-content of 10.9%, a V content of 3.4% and an Al content of 10.1%. The tablets, at a cylinder height of 5 mm and a diameter of 5 mm, had a compressive strength of 109 N on the curved cylinder surface and an internal surface area of 81 m$^2$/g. The 4-O-β-D-galactopyranosyl-α-D-sorbitol produced in a vacuum crystallizer had a purity of ≧99.6%. The content of unreacted 4-O-β-D-galactopyranosyl-α-D-glucopyranose was 0.1%. The sorbitol content was 0.1%. 4-O-β-D-Galactopyranosyl-D-mannitol and mannitol were not detected. Ni, Zr, V and Al contents were each <2 ppm. The activity of the catalyst was still undiminished after a running time of 2016 hours.

Example 12

A high-pressure tube as in Example 1 was packed with 1.41 l of a hydrogenation catalyst produced by tableting metal powder of an alloy of Ni/Zr/Ti having a Zr content of 8.1% and a Ti content of 5.8%, which hydrogenation catalayst, at a cylinder height of 5 mm and a diameter of 5 mm, had a compressive strength of 103 N on the curved cylinder surface and an internal surface area of 81 m$^2$/g. Through this tube, 400 ml of a 50% strength aqueous solution of 4-O-α-D-glucopyranosyl-α-D-glucopyranose in demineralized oxygen-free drinking water having a pH of 7.0 were continuously pumped per hour ascending from bottom to top, together with ten times the molar amount of high-purity hydrogen at a pressure of 300 bar. Aqueous solution and hydrogen were passed beforehand together through a heat exchanger and heated in such a manner that they entered the high-pressure tube at a temperature of 60° C. The mixture of aqueous solution and excess hydrogen leaving the high-pressure tube was passed through a separator, from where the hydrogen, after replacement of the amount consumed, was pumped back into the preheater together with fresh 4-O-α-D-glucopyranosyl-α-D-glucopyranose, and from there was pumped back into the high-pressure tube. The colorless and clear aqueous solution was depressurized and concentrated in a falling-film evaporator to a sugar alcohol content of 80% and then crystallized after further evaporation in a vacuum crystallizer with cooling and, if appropriate, addition of seed crystals. The crystalline 4-O-α-D-glucopyranosyl-α-D-sorbitol had a purity of ≧99.6%. The content of non-hydrogenated 4-O-α-D-glucopyranosyl-α-D-glucopyranose was ≦0.1%. The content of sorbitol was ≦0.1%. Mannitol was not detected. The activity of the catalyst was unchanged even after a running time of 1612 hours.

Example 13

Through a high-pressure tube as in Example 1 was passed in the reverse direction of reaction flow as in Example 1 in the opposite direction to the ascending solution of 4-O-α-D-glucopyranosyl-α-D-glucopyranose, the hydrogen at a temperature of 65° C. and a hydrogen pressure of 250 bar, the same amount as in Example 1 of 45% strength aqueous solution of 4-O-α-D-glucopyranosyl-α-D-glucopyranose which had a pH of 6.5 being hydrogenated per hour. The catalyst was produced by tableting Ni/Zr/Al powder having a Zr content of 14.9% and an Al content of 10.5%. The tablets, at a cylinder height of 5 mm and a diameter of 5 mm, had a compressive strength of 75 N on the curved cylinder surface and an internal surface area of 81 m²/g. After a running time of 1418 hours with undiminished activity, the content of 4-α-D-glucopyranosyl-α-D-sorbitol of the reaction mixture evaporated to dryness in a rotary evaporator was 99.8%. The content of non-hydrogenated 4-O-α-D-glucopyranosyl-α-D-glucopyranose was ≦0.1%. The content of sorbitol was ≦0.1%.

Example 14

In a high-pressure tube as in Example 1, the same amount of a 45% strength aqueous solution of 4-O-α-D-glucopyranosyl-α-D-glucopyranose which had a pH of 7.5 was hydrogenated per hour in the same manner as in Example 1 at a temperature of 60° C. and a hydrogen pressure of 300 bar. The catalyst was produced by tableting a pulverized Ni/Fe/Zr alloy having an Fe content of 5% and a Zr content of 10.9%. The tablets, at a cylinder height of 5 mm and a diameter of 5 mm, had a compressive strength, of 103 N on the curved cylinder surface and an internal surface area of 95 m²/g. The 4-O-α-D-glucopyranosyl-α-D-sorbitol produced in a vacuum evaporator had a purity of 99.7%. The content of unreacted 4-O-α-D-glucopyranosyl-α-D-glucopyranose was 0.1%. The sorbitol content was 0.2%. Ni, Fe and Zr contents were <3 ppm. The activity of the catalyst was unchanged after a running time of 1604 hours.

Example 15

In a high-pressure tube as in Example 1, the same amount of a 40% strength aqueous solution of 4-O-α-D-glucopyranosyl-α-D-glucopyranose which had a pH of 6.5 was hydrogenated in the same manner as in Example 1 at a temperature of 65° C. and a hydrogen pressure of 200 bar. The catalyst was produced by tableting a metal powder of an Ni/Zr/V/Al alloy having a Zr content of 14.9%, a V content of 6.4% and an Al content of 10.4%. The tablets, at a cylinder height of 5 mm and a diameter of 5 mm, had a compressive strength of 95 N on the curved cylinder surface and an internal surface area of 88 m²/g. The 4-O-α-D-glucopyranosyl-α-D-sorbitol produced in a rotary vacuum tube had a purity of ≧99.6%. The content of unreacted 4-O-α-D-glucopyranosyl-α-D-glucopyranose was ≦0.1%. The sorbitol content was 0.1%. The activity of the catalyst was undiminished after a running time of 3128 hours.

What is claimed is:

1. A process for the preparation of epimer-free sugar alcohols selected from the group consisting of xylitol, sorbitol, 4-O-β-D-galactopyranosyl-α-D-sorbitol and 4-O-α-D-glucopyranosyl-α-D-sorbitol by catalytic hydrogenation of the corresponding sugars D-xylose, α-D-glucose, 4-O-β-D-galactopyranosyl-α-D-glucopyranose and 4-O-α-D-glucopyranosyl-α-D-glucopyranose, respectively, in aqueous solution with hydrogen under elevated pressure and at elevated temperature, which comprises carrying out the hydrogenation continuously at a hydrogen pressure of 100 to 400 bar, and temperatures of 20 to 70° C., in the fixed-bed process in a reaction zone on shaped bodies which serve as hydrogenation catalysts and have a compressive strength of 20 to 220 N, and an internal surface area of 10 to 100 m²/g made of (i) one or more elements of the iron subgroup of subgroup VIII of the Periodic Table of the Elements (Mendeleev) which is (are) additionally alloyed with (ii) activating elements of subgroup IV and/or subgroup V.

2. The process of claim 1, wherein the shaped bodies are cylindrical or spherical and have diameters of 2 to 10 mm.

3. The process of claim 2, wherein the shaped bodies have diameters of 3 to 7 mm.

4. The process of claim 1, wherein the hydrogenation of the sugars is carried out in 40 to 60% strength aqueous solution at a pH of 4.5 to 11.5.

5. The process of claim 1, wherein the shaped bodies serving as catalysts have a compressive strength of 70 to 140 N.

6. The process of claim 1, wherein a hydrogen pressure of 150–300 bar is employed.

7. The process of claim 1, wherein a temperature of 40 to 65° C. is employed.

8. The process of claim 1, wherein the shaped bodies serving as catalysts include one or more metals of the iron subgroup at at least 50% by weight, based on the total weight of the shaped bodies.

9. The process of claim 8, wherein the shaped bodies include one or more metals of the iron subgroup at at least 60% by weight, based on the total weight of the shaped bodies.

10. The process of claim 9, wherein the shaped bodies include one or more metals of the iron subgroup at at least 70% by weight, based on the total weight of the shaped bodies.

11. The process of claim 1, wherein the shaped bodies serving as catalysts include one or more metals of subgroups IV and V of the Periodic Table of the Elements at at least 1.5% by weight, based on the total weight of the shaped bodies.

12. The process of claim 11, wherein the shaped bodies include one or more metals of subgroups IV and V at at least 3% by weight, based on the total weight of the shaped bodies.

13. The process of claim 12, wherein the shaped bodies ionclude one or more metals of subgroups IV and V at at least 6% by weight, based on the total weight of the shaped bodies.

14. The process of claim 1, wherein the shaped bodies serving as catalysts include one or more metals of subgroups IV and V at at most 30% by weight, based on the total weight of the shaped bodies.

15. The process of claim 14, wherein the shaped bodies include one or more metals of subgroups IV and V at at most 20% by weight, based on the total weight of the shaped bodies.

16. The process of claim 15, wherein the shaped bodies include one or more metals of subgroups IV and V at at most 15% by weight, based on the total weight of the shaped bodies.

17. The process of claim 1, wherein the shaped bodies serving, as catalysts include one or more catalytically inactive metals in an amount of at most 20% by weight, based on the total weight of the shaped bodies.

18. The process of claim 17, wherein the shaped bodies serving as catalysts include one or more catalytically inactive metals in an amount of at most 15% by weight, based on the total weight of the shaped bodies.

* * * * *